United States Patent [19]

Kondo et al.

[11] Patent Number: 5,245,018
[45] Date of Patent: Sep. 14, 1993

[54] PROCESS FOR PREPARING A RADIOPHARMACEUTICAL COMPOSITION

[75] Inventors: Susumu Kondo, Ichihara; Sakae Okano, Kimitsu; Makoto Azuma, Ichihara, all of Japan

[73] Assignee: Nihon Medi-Physics Co., Ltd., Hyogo, Japan

[21] Appl. No.: 783,776

[22] Filed: Oct. 29, 1991

[30] Foreign Application Priority Data

Oct. 31, 1990 [JP] Japan ................... 2-296563

[51] Int. Cl.$^5$ ............... A61K 43/00; A61K 49/02
[52] U.S. Cl. ............................... 534/14; 424/1.1
[58] Field of Search ....................... 424/1.1; 534/14

[56] References Cited

U.S. PATENT DOCUMENTS

| | | | |
|---|---|---|---|
| 4,489,053 | 12/1984 | Azuma et al. | 424/1.1 |
| 4,510,125 | 4/1985 | Grogg et al. | 424/1.1 |
| 4,638,051 | 1/1987 | Burns et al. | 424/1.1 X |
| 4,849,511 | 7/1989 | Verbruggen | 534/14 |
| 4,883,862 | 11/1989 | Chervu et al. | 530/331 |
| 4,925,650 | 5/1990 | Nosco et al. | 424/1.1 |
| 4,980,147 | 12/1990 | Fritzberg et al. | 424/1.1 |

FOREIGN PATENT DOCUMENTS

| | | |
|---|---|---|
| 0074429 | 3/1983 | European Pat. Off. |
| 0081193 | 6/1983 | European Pat. Off. |
| 0111415 | 6/1984 | European Pat. Off. |
| 0173424 | 3/1986 | European Pat. Off. |
| 0250013 | 12/1987 | European Pat. Off. |
| 0427360 | 5/1991 | European Pat. Off. ............. 424/1.1 |
| 91/16076 | 10/1991 | PCT Int'l Appl. .................. 424/1.1 |

OTHER PUBLICATIONS

Taylor, A., et al, J. Nucl. Med., 27, 795-803 (1986).
Fritzberg, A. R., et al, J. Nucl. Med. 27, 111-116 (1986).
Nosco, D. L., et al, The 8th International Symposium on Radiopharmaceutical Chemistry, Abstract which was circulated at symposium, 1990.
Nosco, D. L., et al, The Journal of Labelled Compounds and Radiopharmaceuticals, XXX, p. 6 (Jan. 1991).

*Primary Examiner*—Robert L. Stoll
*Assistant Examiner*—John M. Covert

[57] ABSTRACT

A process for preparing a radiopharmaceutical composition comprising a technetium 99m chelate complex, comprises the steps of:

(1) mixing (a) $HSCH_2CO-NHCH_2CO-NHCH_2CO-NHCH_2COOH$ (mercaptoacetylglycylglycylglycine, MAG3), (b) a watersoluble reducing agent, (c) a water-soluble stabilizing agent in an amount of not less than 70 mol per 1 mol of the water-soluble reducing agent and (d) a pertechnetate at a pH of about 8 to 11; and (2) heating the resultant mixture at a temperature of about 90 to 140° C.

Said process removes any troublesome labeling operation at the diagnostic site and relieve the practitioners from the exposure to radiation during the labeling operation.

3 Claims, No Drawings

PROCESS FOR PREPARING A RADIOPHARMACEUTICAL COMPOSITION

The present invention relates to a process for preparing a radiopharmaceutical composition. More particularly, it relates to an improved process for preparing a radiopharmaceutical composition comprising a technetium chelate complex suitable for diagnosis of renal function.

Kidneys are important organs responsible for regulation of the compositions of body fluids. Their fundamental constituting unit is called "nephron", and in case of human kidneys, each kidney comprises about one million nephrons. The constancy of a body fluid composition can be maintained by various functions of nephrons such as filtration, passive secretion, active secretion, reabsorption, etc. When a kidney is damaged due to any reason, those functions are lowered or stopped. For evaluation of the extent and/or type of the damage in a kidney, various diagnostic methods for testing renal functions have been devised.

One of such renal function tests is known as a dynamic renal function imaging study. This procedure has conventionally involved the intravenous injection of a radioactively labeled iodine substance such as iodine-131 labeled orthoiodohippurate (hereinafter referred to as "I-131-OIH"). After intravenous injection, I-131-OIH is effectively removed from the blood by active tubular secretion in addition to glomerular filtration at nephrons. As the result, the location and movement of the radiolabeled substance can be detected and analyzed by a gamma-scintillation camera so that the renal function becomes known. While the diagnosis with I-131-OIH is quite useful in evaluation of renal function, it has some serious drawbacks.

First, the energy of gamma rays emitted from I-131 is so high as 364 keV (emission rate, 81%), and therefore the spatial resolution of an image obtained by a gamma-scintillation camera is low. Because of this reason, the minute structure in a kidney is imaged indefinitely, and the useful information are limited. Second, I-131 is a beta-ray emitting nuclide, and the absorbed dose in the surrounding tissues is relatively large. In particular, free I-131 accompanied with I-131-OIH is apt to be accumulated in a thyroid gland so that the absorbed dose in the thyroid gland cannot be ignored. Because of this reason, the maximum dose of I-131-OIH is limited to such a low dose as about 200 to 300 $\mu$Ci. This low dose requires a considerable time of data collection for obtaining an image by a gamma-scintillation camera, and the temporal resolution of the sequential image as obtained during the examination of renal function is lowered.

As a radiolabeled substance overcoming the above drawbacks inherently present in I-131-OIH, Fritzberg et al. proposed the use of technetium-99m labeled mercaptoacetylglycylglycylglycine (hereinafter referred to as "Tc-99m-MAG3") (Fritzberg et al: J.Nucl.Med., 27, 111-116 (1986)). Thereafter, Nosco et al. proposed an improved process for preparation of Tc-99m-MAG3 (8th International Symposium on Radiopharmaceutical Chemistry, Abstract (1990)). According to the proposal by Nosco et al., Tc-99m-MAG3 is prepared by adding an aqueous solution of Tc-99m in the form of sodium pertechnetate to an aqueous solution containing benzoylmercaptoacetylglycylglycylglycine, stannous chloride and sodium tartrate, or its freeze-dried product, introducing air into the resultant mixture to oxidize excessive stannous chloride and heating the resultant solution in a boiled water bath for about 10 minutes.

The thus prepared Tc-99m-MAG3 is said to show substantially the same behavior in vivo (e.g. active secretion into tubules) as I-131-OIH. Thus, the substantially same information as given by I-131-OIH are obtainable by Tc-99m-MAG3 on the diagnosis of renal function. Further, the energy of gamma-rays emitted by Tc-99m as the labeling nuclide in Tc-99m-MAG3 is so low as 140 keV, and the spatial resolution of the image obtained through a gamma-scintillation cameras is greatly improved in comparison with that in case of I-131-OIH. Furthermore, Tc-99m emits only gamma-rays, and the absorbed dose in the surrounding tissues is drastically reduced in comparison with I-131-OIH. The maximum dose would be thus increased to about 100 times that of I-131-OIH. Such high dose enables remarkable shortening of the data collection time on imaging by the use of a gamma-scintillation camera, and as the result, the temporal resolution of the sequential image as obtained during the examination on renal function is significantly increased.

This TC-99m-MAG3, however, requires such troublesome operations as heating and air oxidation on its preparation, and physicians are unfavorably exposed to a great amount of radiation. In order to avoid such exposure, the supply of Tc-99m-MAG3 as an injectable radiopharmaceutical composition, i.e. in the form of a labeled preparation, is considered. But, such supply necessitates the preparation of the injection using radioactivity in an amount of about 10 times in comparison with the preparation by the physicians at the diagnostic or clinical site, because a considerable time is needed for the transportation. Further, the injectable radiopharmaceutical composition must have a sufficient stability to retain a satisfactory radiochemical purity until its delivery to the physicians.

In the examination of renal function, a rapid dynamic trace in early phase after the administration is important, and for this purpose, the intravenous bolus injection is usually requested. For the intravenous bolus injection, the use of a smaller liquid amount is favorable, but Tc-99m-MAG3 as prepared by Nosco et al. only remains stable for 6 hours after preparation when Tc-99m is used in an amount of not more than 100 mCi (8th International Symposium on Radiopharmaceutical Chemistry). In addition, it is reported that in order to prevent decrease of the radiochemical purity, the labelling should be effected in an amount of not less than 4 ml.

For the supply of Tc-99m-MAG3 in an injectable radiopharmaceutical composition, it is thus necessary to provide a process wherein labelling can be effected with a larger amount of radioactivity and which affords the product with excellent stability. It is also necessary that the product is obtainable in a higher radiochemical purity with a smaller liquid amount, i.e. in a higher radioactivity concentration.

As the result of an extensive study, it has now been found that an injectable radiopharmaceutical composition comprising Tc-99m-MAG3 as prepared by a certain specific procedure overcomes the drawbacks as stated above and is quite useful for examination of renal function. The present invention is based on the above finding.

According to the present invention, a radiopharmaceutical composition comprising Tc-99m-MAG3 is prepared by (1) mixing (a) HSCH2CO-NHCH2CO- NHCH2CO-NHCH-2COOH (mercaptoacetylglycyl-glycylglycine, MAG3), (b) a water-soluble reducing agent, (c) a water-soluble stabilizing agent in an amount of not less than 70 mol per 1 mol of the watersoluble reducing agent and (d) a Tc-99m pertechnetate at a pH of about 8 to 11 and (2) heating the resultant mixture at a temperature of about 90 to 140° C.

One of the significant characteristics in the process of the invention is that MAG3 is used as such without protection of the terminal thiol group by any protective group as benzoyl, which is essential in the processes of Fritzberg et al. and Nosco et al. Another characteristic is that, different from the processes of Fritzberg et al. and Nosco et al., the process of the invention uses a large amount of a water-soluble stabilizer in the absence of an exchange ligand such as a citrate or a tartrate and performs heating (usually about 90 to 140° C., preferably about 100 to 120° C.) under an alkaline condition.

The water-soluble reducing agent to be used in the invention may be any pharmaceutically acceptable watersoluble reducing agent, and its preferred examples are primary tin salts, i.e. divalent tin salts. Specific examples are stannous chloride, stannous fluoride, stannous sulfate, stannous nitrate, stannous acetate, stannous citrate, stannous tartrate, etc.

As the water-soluble stabilizer, there may be used ascorbic acid or erythrobic acid, or any pharmaceutically acceptable salt or ester thereof. The amount of such stabilizer is normally in an amount of not less than about 70 mol, preferably 100 mol, to 1 mol of the reducing agent, although there is no upper limit to the amount of the stabilizer insofar as any material toxicity or pharmacological effect is not exerted.

The radioactive diagnostic composition of the invention may be formulated in any appropriate preparation form such as powder, lyophilized powder or solution. Further, it may comprise, in addition to said essential components, any auxiliary agent such as a pH regulating agent (e.g. acid, base), an isotonic agent (e.g. sodium chloride), a preservative (e.g. benzyl alcohol) or the like.

Practical embodiments of the invention will be hereinafter explained in details by way of examples.

Example 1

Preparation of a non-radioactive carrier composition-:

The following operations were all conducted in a stream of an inert gas (e.g. nitrogen, argon) under sterile conditions.

Sterile and pyrogen free water was purged with an inert gas (e.g. argon) to remove oxygen dissolved therein. Into 1000 ml of this water, sodium L-(+)-ascorbate and mercaptoacetylglycylglycylglycine (MAG3) (658 mg) were dissolved, and anhydrous stannous chloride (57 mg) was added thereto, followed by adjustment of pH with addition of aqueous sodium hydroxide solution. The resultant solution having a sodium L-(+) ascorbate concentration of 0 to 80 mM and a pH of 7.5 to 11.0 was filtered through a membrane filter (pore size, 0.22 μm), and 0.5 ml each was filled in a vial. The aqueous composition was stored as such, in a freezed state or in a freeze-dried state to use as a nonradioactive carrier composition.

Example 2

Preparation of a radiopharmaceutical composition comprising Tc-99m-MAG3-:

The aqueous composition (0.5 ml) as obtained in Example 1 was mixed with a physiological saline solution (1.5 ml) containing Tc-99m in the form of sodium pertechnetate. The resultant mixture was stirred and heated in an autoclave at 120° C. for 30 minutes, followed by cooling to room temperature in a water bath to give a radiopharmaceutical composition comprising Tc-99m-MAG 3. With variation of the radioactivity of Tc-99m in the physiological saline solution, there was obtained a radiopharmaceutical composition containing Tc-99m-MAG3 of different radioactivity (5 to 130mCi on labeling).

Example 3

Analysis of a radiopharmaceutical composition comprising Tc-99m-MAG3-:

Analysis of Tc-99m-MAG3 may be carried out by the use of a chromatographic filter paper obtained from Toyo Filter Paper Co., Ltd.

The radiopharmaceutical composition containing Tc-99m-MAG3 obtained in Example 2 was subjected to chromatography (filter paper: Toyo Filter Paper No. 51B; developing solvent: acetonitrile/water =70/30), and the following development was observed: non-combined Tc-99m sodium pertechnetate, Rf = 0.9 to 1.0; Tc-99m tin colloid and/or reduced hydrolyzed technetium such as $TcO_2$, Rf = 0; TC-99m-MAG3, Rf = 0.4; complex of impurities in MAG3 with Tc-99m or complex presumed as Tc-99m-$(MAG3)_2$, Rf = 0.25. On the basis of this development, the radiochemical purity of Tc-99m-MAG3 may be calculated according to the following equation:

Radiochemical purity (%) =

$$\frac{\text{Radioactivity of peak around } Rf = 0.4}{\text{Total radioactivity on filter paper}} \times 100$$

Example 4

Effect of pH on preparation of a radiopharmaceutical composition comprising Tc-99m-MAG3-:

Using the non-radioactive carrier composition prepared as in Example 1, comprising MAG3 (2.5 mM), ascorbic acid (75 mM) and stannous chloride (0.3 mM) and having a pH of 7.5, 8.5, 9.5, 10.0, 10.5 or 11.0 and a physiological saline solution containing 5 mCi of Tc-99m in the form of sodium pertechnetate, there was prepared a radiopharmaceutical composition comprising Tc-99m-MAG3 as in Example 2, which was then subjected to evaluation of the radiochemical purity as in Example 3. The result are shown in Table 1.

The results in Table 1 show that Tc-99m-MAG3 having a higher radiochemical purity is obtainable under alkaline condition and also that Tc-99m-MAG3 of a high radiochemical purity is obtainable without a benzoyl protective group for the terminal thiol group in the ligand MAG3, said benzoyl protective group having been taken as essential in the method of Fritzberg et al method.

TABLE 1

Effect of pH on preparation of Tc-99m-MAH3:-

| pH | 7.5 | 8.5 | 9.5 | 10.0 | 10.5 | 11.0 |
|---|---|---|---|---|---|---|
| Radiochemical purity (%) | 68.4 | 90.3 | 96.5 | 95.3 | 95.9 | 97.1 |

Example 5

Effect of ascorbic acid concentration on stability of a radioapharmaceutical composition comprising Tc-99m-MAG3-:

Using the non-radioactive carrier composition prepated as in Example 1, comprising MAG3 (2.5 mM), ascorbic acid (0, 5, 20, 40 or 80 mM) and stannous chloride (0.3 mM) and having a pH of 10.5 and a physiological saline solution containing 130 mCi of Tc-99m in the form of sodium pertechnetate, there was prepared a radiopharmaceutical composition comprising Tc-99m-MAG3 as in Example 2, which was subjected to evaluation of the radiochemical purity as in Example 3 immediately after the preparation and after shaking at room temperature for 15 hours. The result are shown in Table 2.

The results in Table 2 show that a higher radiochemical purity of Tc-99m-MAG3 is obtainable and can be retained over a long period of time when the molar ratio of ascorbic acid to stannous chloride is about 70 or more.

Still, said shaking at room temperature for 15 hours is comparable to the normal state of transportation from the preparation to the user or customer.

TABLE 2

Effect of ascorbic acid concentration on stability of Tc-99m-MAG3:-

| Ascorbate/$Sn^{2+}$ (molar ratio) | | 0 | 17 | 67 | 133 | 267 |
|---|---|---|---|---|---|---|
| Radiochemical purity (%) | Immediately after preparation | 95.1 | 95.5 | 97.2 | 96.0 | 96.5 |
| | After shaking at room temperature for 15 hours | 85.6 | 91.5 | 94.5 | 94.6 | 94.6 |

Example 6

Effect of heating on preparation of a radiopharmaceutical composition comprising Tc-99m-MAG3-:

Using the non-radioactive carrier composition prepared as in Example 1 (Sample No. 1, 2 or 3 as shown in Table 3) and a physiological saline solution containing 5 mCi of Tc-99m in the form of sodium pertechnetate, there was prepared a radiopharmaceutical composition comprising Tc-99m-MAG3 as in Example 2 (i.e. by heating). Likewise, using the non-radioactive carrier composition prepared as in Example 1 (Sample No. 1', 2' or 3' as shown in Table 3) and a physiological saline solution containing 5 mCi of Tc-99m in the form of sodium pertechnetate, there was prepared a radiopharmaceutical composition comprising Tc-99m-MAG3 by mixing said non-radioactive carrier composition and said physiological saline solution together, stirring the resultant mixture and allowing to stand at room temperature for 1 hour. The thus prepared radiopharmaceutical composition was subjected to evaluation of the radiochemical purity as in Example 3. The results are shown in Table 4.

TABLE 3

| Agent | Tc-99m-MAG3 used for evaluation | | | | | |
|---|---|---|---|---|---|---|
| | 1 | 1' | 2 | 2' | 3 | 3' |
| Concentration of MAG3 (mM) | 2.5 | 2.5 | 2.5 | 2.5 | 2.5 | 2.5 |
| pH | 10.5 | 10.5 | 9.5 | 9.5 | 10.5 | 10.5 |
| Concentration of stannous chloride (mM) | 0.3 | 0.3 | 0.3 | 0.3 | 0.3 | 0.3 |
| Concentration of ascorbic acid (mM) | 0 | 0 | 75 | 75 | 75 | 75 |

TABLE 4

Effect of heating on preparation of Tc-99m-MAG3

| Agent | Heating | | | Allowing to stand at room temperature | | |
|---|---|---|---|---|---|---|
| | 1 | 2 | 3 | 1' | 2' | 3' |
| Radiochemical purity (%) | 95.1 | 96.5 | 95.9 | 14.5 | 13.1 | 90.3 |

The results in Table 4 show that such a high radiochemical purity as 90% can be attained in the presence of ascorbate even allowed to stand at room temperature when the pH is more than 10, but in order to attain a higher radiochemical purity, heating is essential.

Example 7

Biodistribution of a radiopharmaceutical composition comprising Tc-99m-MAG3-:

Using the non-radioactive carrier composition prepared as in Example 1, comprising MAG3 (2.5 mM), ascorbate (85 mM) and stannous chloride (0.17 mM) and having a pH of 10.5 and a physiological saline solution containing 10 mCi of Tc-99m in the form of sodium pertechnetate, there was prepared a radiopharmaceutical diagnostic composition comprising Tc-99m-MAG3 as in Example 2. Immediately after the preparation, the radiochemical purity was determined in the manner as shown in Example 3 to be 98.3%.

The radiopharmaceutical composition (0.2 ml) was administered to each of Sprague-Dawley strain female rats by intravenous injection. After 15 minutes or 1 hour, the animal was sacrificed, and the organs were taken out. The radioactivity of each organ was determined, and the results are shown in Table 5.

As is clear from Table 5, Tc-99m-MAG3 prepared by the method of the invention is rapidly excreted through the kidneys into urine. Tc-99m-MAG3 has thus an excellent property suitable for diagnosis of renal function.

TABLE 5

Biodistribution of Tc-99m-MAG3 in rats

| Organ | After 15 minutes | After 1 hour |
|---|---|---|
| Blood | 2.70 | 0.25 |
| Lung | 1.84 | 0.10 |
| Kidney | 14.65 | 0.82 |
| Stomach | 0.07 | 0.02 |
| Intestines | 5.12 | 5.74 |
| Urine | 65.74 | 90.56 |

Note:
Numbers expressed as percentage (%) to total radioactivity administered.

As understood from the above, Tc-99m-MAG3 useful as a diagnostic agent for renal function can be prepared from mercaptoacetylglycylglycylglycine not having a benzoyl protective group on the terminal thiol group without losing its excellent property. It is notable that such preparation is possible even when a water-soluble stabilizing agent is used in such a large amount as 70 mol or more to one mol of a water-soluble reducing agent. It is also notable that the use of a water-soluble stabilizing agent in such a large amount makes it possible to retain the stability over a long period of time.

Accordingly, the present invention enables the supply of a radiopharmaceutical composition comprising Tc-99m-MAG3 useful as a diagnostic agent for renal function to physicians without any troublesome labeling operation at the diagnostic site. Therefore, physicians can be relieved from the exposure to radiation during the labeling operation. Further, this invention makes it possible to minimize the liquid amount of the injection to be administered to 2 ml or less. Administration of such small amount is quite favorable for diagnosis of renal function, which usually requires rapid intravenous bolus injection.

What is claimed is:

1. A process for preparing a radiopharmaceutical composition comprising a technetium 99m chelate complex, comprises the steps of:
   (1) mixing (a) $HSCH_2CO-NHCH_2CO-NHCH_2CO-NHCH_2COOH$ (mercaptoacetylgycylglycylglycine, MAG3), (b) a water-soluble reducing agent, (c) a water-soluble stabilizing agent for the reduced technetium present in the reaction medium, in an amount of from about 70 mol to 100 mol per 1 mol of the water-soluble reducing agent and (d) a pertechnetate at a pH of about 8 to 11 in the absence of any exchange ligand; and
   (2) heating the resultant mixture at a temperature of about 90 to 140° C.

2. The process according to claim 1, wherein the water-soluble reducing agent is a stannous salt.

3. The process according to claim 1, wherein the water-soluble stabilizing agent is any one selected from the group consisting of ascorbic acid and erythorbic acid, and their pharmaceutically acceptable salts and esters.

* * * * *